United States Patent [19]

Dutra et al.

[11] 4,238,218

[45] Dec. 9, 1980

[54] ETHANIMIDOTHIOIC (α-DIARYLOXYPHOSPHINYLME-THYLAMINO) ACID ESTER HYDROCHLORIDES, HERBICIDAL COMPOSITION AND HERBICIDAL USE THEREOF

[75] Inventors: Gerard A. Dutra, Ladue; James A. Sikorski, University City, both of Mo.

[73] Assignee: Monsanto Company, St. Louis, Mo.

[21] Appl. No.: 913,167

[22] Filed: Jun. 6, 1978

[51] Int. Cl.³ .................... A01N 57/12; A01N 57/14; C07F 9/40
[52] U.S. Cl. ........................................ 71/87; 260/944
[58] Field of Search ...................... 260/944; 71/87, 86

[56] References Cited

U.S. PATENT DOCUMENTS

| | | | |
|---|---|---|---|
| 3,799,758 | 3/1974 | Franz | 71/86 |
| 4,067,719 | 1/1978 | Dutra | 71/87 |
| 4,104,050 | 8/1978 | Dutra | 260/944 |
| 4,137,064 | 11/1979 | Trueb | 71/86 |

Primary Examiner—Catherine L. Mills
Attorney, Agent, or Firm—William T. Black; Donald W. Peterson

[57] ABSTRACT

This disclosure relates to ethanimidothioic acid ester hydrochlorides. More particularly, this disclosure relates to novel (α-diaryloxyphosphinylmethylamino) ethanimidothioic hydrocarbon ester hydrochlorides, herbicidal compositions containing such thioimidate hydrochlorides and the herbicidal use thereof.

24 Claims, No Drawings

ETHANIMIDOTHIOIC (α-DIARYLOXYPHOSPHINYLMETHYLAMINO) ACID ESTER HYDROCHLORIDES, HERBICIDAL COMPOSITION AND HERBICIDAL USE THEREOF

This invention relates to ethanimidothioic acid ester hydrochlorides. More particularly, this invention is concerned with the novel phosphinylmethylamino substituted ethanimidothioic ester hydrochlorides and the novel herbicidal compositions containing the same and the herbicidal use thereof.

(Diaryloxyphosphinylmethylamino)glycinonitriles are known to be active post-emergent herbicides. These compounds are shown in U.S. Pat. No. 4,067,719. It is also known that these compounds can be converted to N-phosphonomethylglycine by hydrolysis with aqueous hyrochloric acid. N-phosphonomethylglycine is an excellent post-emergent herbicide as is known from U.S. Pat. No. 3,799,758. In application Ser. No. 807,953, filed June 20, 1977, it is disclosed that acetimidic diaryloxyphosphinylmethylamino acid ester hydrochlorides also have herbicidal activity.

It has now been discovered that novel ethanimidothioic (α-diaryloxyphosphinylmethylamino) acid ester hydrochlorides can be produced by the reaction of (diaryloxyphosphinylmethylamino)glycinonitriles with thiols or phenylthiols and hydrogen chloride under anhydrous conditions employing a solvent.

The novel thioimidate ester compounds of this invention have the formula

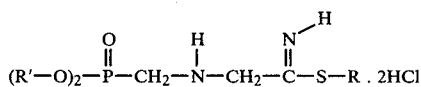

wherein R is selected from the group consisting of primary or secondary alkyl containing up to 10 carbons; phenyl; phenyl substituted with one or two groups individually selected from the class consisting of lower alkyl, lower alkoxy, halogen, nitro and trifluoromethyl; and lower alkyl substituted with naphthyl, phenyl or phenyl substituted with one or two groups individually selected from the class consisting of lower alkyl, lower alkoxy, halogen, nitro and trifluoromethyl; and R' is phenyl, biphenyl, naphthyl, or a lower alkyl substituted phenyl or naphthyl group.

As employed herein, the term "lower" designates those radicals which contain up through four carbon atoms in a straight or branched chain.

Illustrative of the primary or secondary alkyl radicals which R represents are, for example, methyl, ethyl, propyl, butyl, isopropyl, isobutyl, octyl, decyl and the like.

Illustrative of the radicals substituted on the phenyl and on the phenyl of the phenylalkyl groups which R represents are, for example, lower alkyl such as methyl, ethyl, propyl or butyl; lower alkoxy such as methoxy, ethoxy, propoxy or butoxy; fluoro, chloro, bromo or iodo; nitro; trifluoromethyl; and the like.

Illustrative of the lower alkyl substituted phenyl and naphthyl groups which R' represents include o-, m- and p-tolyl, xylyl, mesityl, ethylphenyl, isopropylphenyl, butylphenyl, α- and β-methylnaphthyl, α- and β-ethylnaphthyl and the like.

In accordance with this invention, the ethanimidothioic acid esters of N-phosphonomethylglycinonitrile are produced under anhydrous conditions by dissolving N-phosphonomethylglycinonitrile in methylene chloride and then adding thereto a thiol followed by subsequent bubbling of gaseous hydrogen chloride through the resultant solution. It is necessary at all times to maintain the temperature in a range sufficient to initiate and maintain the reaction. This procedure is best illustrated by the following reaction scheme:

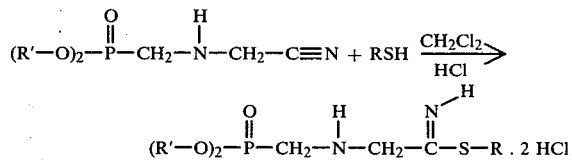

It is preferred to employ an excess of the thiol in order to insure maximum recovery of the ethanimidothioic acid ester. The process can be conducted within a temperature range of −20° C. to +10° C. The compounds of this invention are sensitive to heat and moisture and should, therefore, be stored under anhydrous conditions in a cool place.

The starting cyanomethylaminomethylphosphonic acid esters are prepared by reacting a diaryl phosphite such as diphenyl, ditolyl, dixylyl, di(biphenyl) or dinaphthyl phosphite with s-tri(cyanomethyl)hexahydrotriazine.

The following illustrative, non-limiting examples will serve to further demonstrate to those skilled in the art the manner in which specific compounds within the scope of this invention can be prepared. In the examples, all parts are parts by weight unless otherwise expressly stated.

EXAMPLE I

N-diphenoxyphosphonomethylglycinonitrile (6.04 g., 0.02 mol.) was dissolved in approximately 100 ml. of dry methylene chloride in a three-necked flask equipped with a nitrogen inlet, gas sparge, stir bar and thermometer. After the resulting solution was cooled to −10° C., ethanethiol (2.5 g., 0.04 mol.) was added to the mixture. Gaseous hydrogen chloride was then bubbled into the cold solution for 90 minutes. The reaction mixture was stirred at −10° C. for 2 hours. The white precipitate which had formed was filtered under nitrogen and yielded 6.0 g. (69% yield) of a white solid identified as ethanimidothioic acid, 2-[(diphenoxyphosphinylmethyl)amino]-S-ethyl ester, dihydrochloride having a melting point of 112°–113° C. and the following analysis:

CALCULATED: C, 46.69; H, 5.30; N, 6.41; Cl, 16.21; FOUND: C, 46.47; H, 5.32; N, 6.34; Cl, 16.04.

EXAMPLE II

N-diphenoxyphosphonomethylglycinonitrile (6.04 g., 0.02 mol.) was dissolved in approximately 200 ml. of dry methylene chloride in a three-necked flask equipped with a nitrogen inlet, gas sparge, stir bar and thermometer. After the resulting solution was cooled to −10° C., thiophenol (4.54 g., 0.04 mol.) was added to the mixture. Gaseous hydrogen chloride was then bubbled into the cold solution (−10° to −20° C.) for 1 hour. The reaction mixture was stirred at −5° to +5° C. for 16 hours. The white precipitate which had formed was filtered under nitrogen and yielded 8.05 g. (83% yield) of a white solid identified as ethanimidothioic acid, 2-[(diphenoxyphosphinylmethyl)amino]-S-phenyl ester, dihydrochloride having a melting point of 103°–105° C. and the following analysis:

CALCULATED: C, 51.97; H, 4.78; N, 5.77; S, 6.61; Cl, 14.61; FOUND: C, 51.89; H, 4.76; N, 5.79; S, 6.64; Cl, 14.49.

EXAMPLE III

N-diphenoxyphosphonomethylglycinonitrile (6.04 g., 0.02 mol.) was dissolved in approximately 150 ml. of dry methylene chloride in a three-necked flask equipped with a nitrogen inlet, gas sparge, stir bar and thermometer. After the resulting solution was cooled to $-10°$ C., benzyl mercaptan (4.99 g., 0.04 mol.) was added to the mixture. Gaseous hydrogen chloride was then bubbled into the cold solution for 1 hour. The reaction mixture was stirred at $-10°$ C. for 16 hours. The white precipitate which had formed was filtered under nitrogen, washed with methylene chloride and yielded 3.1 g. (31% yield) of a white solid identified as ethanimidothioic acid, 2-[(diphenoxyphosphinylmethyl)amino]-S-benzyl ester, dihydrochloride having a melting point of 86°–92° C. and the following analysis:

CALCULATED: C, 52.91; H, 5.05; N, 5.61; FOUND: C, 52.75; H, 5.05; N, 5.59.

EXAMPLE IV

N-diphenoxyphosphonomethylglycinonitrile (6.04 g., 0.02 mol.) and p-chlorothiophenol (5.8 g., 0.04 mol.) were dissolved in approximately 200 ml. of dry methylene chloride in a three-necked flask equipped with a nitrogen inlet, gas sparge, stir bar and thermometer. After the resulting solution was cooled to $-10°$ C., gaseous hydrogen chloride was then bubbled into the cold solution ($-10°$ C.) for 90 minutes. The reaction mixture was stirred at $-10°$ to $+10°$ C. for 64 hours. The white precipitate which had formed was filtered under nitrogen, washed several times with methylene chloride and yielded 2.5 g. (24% yield) of a white solid identified as ethanimidothioic acid, 2-[(diphenoxyphosphinylmethyl)amino]-S-4-chlorophenyl ester, dihydrochloride having a melting point of 89°–91° C. and the following analysis:

CALCULATED: C, 46.90; H, 4.50; N, 5.21; FOUND: C, 47.03; H, 4.24; N, 5.54.

EXAMPLE V

N-diphenoxyphosphonomethylglycinonitrile (6.04 g., 0.02 mol.) and p-nitrothiophenol (6.2 g., 0.04 mol.) were dissolved in approximately 200 ml. of dry methylene chloride in a three-necked flask equipped with a nitrogen inlet, gas sparge, stir bar and thermometer. After the resulting solution was cooled to $-10°$ C., gaseous hydrogen chloride was then bubbled into the cold solution for 90 minutes. The reaction mixture was stirred at $-10°$ C. for 16 hours. The white precipitate which had formed was filtered under nitrogen, washed several times with methylene chloride and yielded 4.5 g. (42% yield) of a white solid identified as ethanimidothioic acid, 2-[(diphenoxyphosphinylmethyl)amino]-S-4-nitrophenyl ester, dihydrochloride having a melting poin of 69°–72° C. and the following analysis:

CALCULATED: C, 47.56; H, 4.18; N, 7.92; FOUND: C, 47.30; H, 4.27; N, 7.89.

EXAMPLE VI

N-diphenoxyphosphonomethylglycinonitrile (6.04 g., 0.02 mol.) was dissolved in approximately 150 ml. of methylene chloride in a three-necked flask equipped with a nitrogen inlet, gas sparge, stir bar and thermometer. After the resulting solution was cooled to $-10°$ C., p-chlorobenzyl mercaptan (6.35 g., 0.04 mol.) was added to the mixture. Gaseous hydrogen chloride was then bubbled into the cold solution for 90 minutes. The reaction mixture was stirred at $-10°$ C. for 16 hours. The white precipitate which had formed was filtered under nitrogen and yielded 5.5 g. (52% yield) of white solid identified as ethanimidothioic acid, 2-[(diphenoxyphosphinylmethyl) amino]-S-4-chlorobenzyl ester, dihyrochloride having a melting point of 87°–90° C. and the following analysis:

CALCULATED: C, 48.41; H, 4.68; N, 5.13; FOUND: C, 48.13; H, 4.47; N, 5.12.

EXAMPLE VII

N-diphenoxyphosphonomethylglycinonitrile (6.04 g., 0.02 mol.) was dissolved in approximately 150 ml. of dry methylene chloride in a three-necked flask equipped with a nitrogen inlet, gas sparge, stir bar and thermometer. Phenylethyl mercaptan (5.52 g., 0.04 mol.) was then added to the mixture and the resultant solution was cooled to $-10°$ C. Gaseous hydrogen chloride was then bubbled into the cold solution for 90 minutes. The reaction mixture was stirred at $-10°$ C. for 16 hours. The white precipitate which had formed was filtered under nitrogen and yielded 9.2 g. (90% yield) of a white solid identified as ethanimidothioic acid, 2-[(diphenoxyphosphinylmethyl)amino]-S-(2-phenyl) ethyl ester, dihydrochloride having a melting point of 107°–109° C. and the following analysis:

CALCULATED: C, 52.88; H, 5.40; N, 5.36; S, 6.14; Cl, 13.57; FOUND: C, 52.69; H, 5.29; N, 5.38; S, 6.04; Cl, 13.45.

EXAMPLE VIII

N-diphenoxyphosphonomethylglycinonitrile (6.04 g., 0.02 mol.) was dissolved in approximately 150 ml. of dry methylene chloride in a three-necked flask equipped with a nitrogen inlet, gas sparge, stir bar and thermometer. m-Trifluoromethylthiophenol (10.0 g.) was then added to the mixture and the resultant solution was cooled to $-10°$ C. Gaseous hydrogen chloride was then bubbled into the cold solution for 90 minutes. The reaction mixture was stirred at $-10°$ C. for 16 hours. The white precipitate which had formed was filtered under nitrogen, washed with methylene chloride and diethyl ether and yielded 6.5 g. (59% yield) of a white solid identified as ethanimidothioic acid, 2-[(diphenoxyphosphinylmethyl)amino]-S-3-trifluoromethylphenyl ester, dihydrochloride having a melting point of 105°–107° C. and the following analysis:

CALCULATED: C, 47.75; H, 4.01; N, 5.05; S, 5.79; Cl, 12.81; FOUND: C, 47.57; H, 4.00; N, 5.24; S, 5.97; Cl, 13.26.

EXAMPLE IX

N-diphenoxyphosphonomethylglycinonitrile (9.06 g., 0.03 mol.) was dissolved in approximately 150 ml. of dry methylene chloride in a three-necked flask equipped with a nitrogen inlet, gas sparge, stir bar and thermometer. After the resulting solution was cooled to $-5°$ C., m-nitrobenzyl mercaptan (10.0 g., 0.06 mol.) was added to the mixture. Gaseous hydrogen chloride was then bubbled into the cold solution for 90 minutes maintaining a temperature of $-10°$ to 0° C. The reaction mixture was stirred at $-5°$ C. for 72 hours. The white precipitate which had formed was filtered under nitrogen, washed with dry methylene chloride and yielded 14.5 g. (89% yield) of ethanimidothioic acid,-2-[(diphenoxyphosphinylmethyl)amino]-S-3-nitrobenzyl ester, dihydrochloride having a melting point of 107°–109° C. and the following analysis:

CALCULATED: C, 48.54; H, 4.44; N, 7.72; Cl, 13.02; FOUND: C, 48.58; H, 4.46; N, 7.73; Cl, 13.02.

EXAMPLE X

N-diphenoxyphosphonomethylglycinonitrile (6.04 g., 0.02 mol.) was dissolved under nitrogen in approximately 150 ml. of dry methylene chloride in a three-necked flask equipped with a nitrogen inlet, gas sparge, stir bar and thermometer. After the resulting solution was cooled to −10° C., α-naphthylmethyl mercaptan (7.3 g., 0.04 mol.) was added to the mixture. Gaseous hydrogen chloride was then bubbled into the cold solution for 90 minutes. The reaction mixture was stirred at −5° C. for 24 hours. The white precipitate which has formed was filtered under nitrogen and yielded 8.8 g. (80% yield) of white solid identified as ethanimidothioic acid,-2-[(diphenoxyphosphinylmethyl)amino]-S-α-naphthylmethyl ester, dihydrochloride having a melting point of 89°–91° C. and the following analysis:

CALCULATED: C, 56.84; H, 4.95; N, 5.10; Cl, 12.90; FOUND: C, 56.90; H, 4.98; N, 5.09; Cl, 12.80.

EXAMPLE XI

N-diphenoxyphosphonomethylglycinonitrile (9.06 g., 0.03 mol.) was dissolved under nitrogen in approximately 200 ml. of dry methylene chloride in a three-necked flask equipped with a nitrogen inlet, gas sparge, stir bar and thermometer. After the resulting solution was cooled to −10° C., p-methoxybenzyl mercaptan (9.69 g., 0.06 mol.) was added to the mixture. Gaseous hydrogen chloride was then bubbled into the cold solution for 90 minutes. The reaction mixture was stirred at −10° to 0° C. for 42 hours. The white precipitate which had formed was filtered under nitrogen, washed with methylene chloride and yielded 11.7 g. (74% yield) of ethanimidothioic acid,-2-[(diphenoxyphosphinylmethyl) amino]-S-4-methoxy benzyl ester, dihydrochloride having a melting point of 99°–101° C. and the following analysis:

CALCULATED: C, 52.18; H, 5.14; N, 5.29; Cl, 13.39; FOUND: C, 52.09; H, 5.15; N, 5.29; Cl, 13.30.

EXAMPLE XII

N-diphenoxyphosphonomethylglycinonitrile (9.06 g., 0.03 mol.) was dissolved under nitrogen in approximately 150 ml. of dry methylene chloride in a three-necked flask equipped with a nitrogen inlet, gas sparge, stir bar and thermometer. After the resulting solution was cooled to −10° C., o-methylbenzyl mercaptan (9.2 g., 0.06 mol.) was added to the mixture. Gaseous hydrogen chloride was then bubbled into the cold solution for 90 minutes. The reaction mixture was stirred at −5° C. for 64 hours. The white precipitate which had formed was filtered under nitrogen, washed with methylene chloride and yielded 6.2 g. (61% yield) of a white solid identified as ethanimidothioic acid,-2-[(diphenoxyphosphinylmethyl)amino]-S-2-methylbenzyl ester, dihydrochloride having a melting poin of 110°–112° C. and the following analysis:

CALCULATED: C, 53.91; H, 5.11; N, 5.47; Cl, 13.84; FOUND: C, 53.18; H, 5.31; N, 5.42; Cl, 13.75.

EXAMPLE XIII

N-diphenoxyphosphonomethylglycinonitrile (3.93 g., 0.013 mol.) was dissolved under nitrogen in approximately 200 ml. of dry methylene chloride in a three-necked flask equipped with a nitrogen inlet, gas sparge, stir bar and thermometer. After the resulting solution was cooled to −10° C., m-trifluoromethyl benzyl mercaptan (5.10 g., 0.026 mol.) was added to the mixture. Gaseous hydrogen chloride was then bubbled into the cold solution for 90 minutes. The reaction mixture was stirred at −5° to +5° C. for 48 hours. The white precipitate which had formed was filtered under nitrogen, washed with methylene chloride and yielded 4.55 g. (62% yield) of a white solid identified as ethanimidothioic acid,-2-[(diphenoxyphosphinyl)amino]-S-3-trifluoromethylbenzyl ester, dihydrochloride having a melting point of 105°–107° C. and the following analysis:

CALCULATED: C, 48.69; H, 4.26; N, 4.94; Cl, 12.50; FOUND: C, 48.60; H, 4.27; N, 4.93; Cl, 12.46.

EXAMPLE XIV

N-diphenoxyphosphonomethylglycinonitrile (6.04 g., 0.02 mol.) was dissolved under nitrogen in approximately 150 ml. of dry methylene chloride in a four-necked flask equipped with a nitrogen inlet, gas sparge, stir bar, thermometer and dry ice condenser. After the resulting solution was cooled to −10° C., methanethiol (15 g., 0.3 mol.) was added to the mixture. Gaseous hydrogen chloride was then bubbled into the cold solution for 90 minutes. The reaction mixture was stirred at −10° C. to 0° C. for 16 hours. The white precipitate which had formed was filtered under nitrogen, washed with dry methylene chloride and diethyl ether and yielded ethanimidothioic acid, 2-[(diphenoxyphosphinylmethyl)amino]-S-methyl ester, dihydrochloride having a melting point of 115°–118° C.

EXAMPLE XV

N-diphenoxyphosphonomethylglycinonitrile (6.04 g., 0.02 mol.) was dissolved under nitrogen in approximately 150 ml. of dry methylene chloride in a three-necked flask equipped with a nitrogen inlet, gas sparge, stir bar and thermometer. After the resulting solution was cooled to −10° C., 2-propanethiol (14.9 g., 0.2 mol.) was added to the mixture. Gaseous hydrogen chloride was then bubbled into the cold solution for 90 minutes. The resulting solution was then stored under nitrogen at −10° C. for 16 hours. The white precipitate which had formed was filtered under nitrogen, washed with dry methylene chloride and diethyl ether and yielded ethaimidothioic acid, 2-[(diphenoxyphosphinylmethyl)amino]-S-isopropyl ester, dihydrochloride having a melting point of 104°–105° C.

Other compounds of the present invention that can be made in general accordance with the foregoing procedures include:

ethanimidothioic acid 2-[(diphenoxyphosphinylmethyl)amino]-S-butyl ester, dihydrochloride
ethanimidothioic acid 2-[(diphenoxyphosphinylmethyl)amino]-S-isobutyl ester, dihydrochloride
ethanimidothioic acid 2-[(diphenoxyphosphinylmethyl)amino]-S-octyl ester, dihydrochloride
ethanimidothioic acid 2-[(diphenoxyphosphinylmethyl)amino]-S-p-methylphenyl ester dihydrochloride

EXAMPLE XVI

The post-emergent herbicidal activity of the compounds of this invention is demonstrated as follows. The active ingredients are applied in spray form to 14 or 21 day old specimens of the various plant species. The spray, a water or solvent solution containing the active ingredient and a surfactant (35 parts butylamine salt of dodecylbenzene sulfonic acid and 65 parts tall oil condensed with ethylene oxide in the ratio of 11 moles ethylene oxide to 1 mole tall oil) is applied to the plants in different sets of pans at several rates (kilograms of active ingredient per hectare), normally in a spray volume of 1871 liters/hectare. In the tables, the examples with letters appearing after the number were prepared in solvents, either acetone (a), or dimethylsulfoxide (b), or tetrahydrofuran (c). The treated plants are placed in a greenhouse and the effects are observed and recorded after approximately 2 or 4 weeks (WAT) as is indicated in the table.

The post-emergent herbicidal index used in the tables is as follows:
0 = 0 to 24% control
1 = 25 to 49% control
2 = 50 to 74% control
3 = 75 to 99% control
4 = 100% kill The plant species employed in the tables are as follows:

| | |
|---|---|
| A - Canada Thistle | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge | Q - Wild Buckwheat |
| H - Quackgrass | R - Hemp Sesbania |
| I - Johnsongrass | S - Panicum Spp |
| J - Downy Brome | T - Crabgrass |

TABLE I

| Compound of Example | WAT | kg/h | A | B | C | D | E | F | G | H | I | J | K |
|---|---|---|---|---|---|---|---|---|---|---|---|---|---|
| I (a) * | 4 | 11.2 | 2 | 3 | 3 | 2 | 4 | 4 | 2 | 3 | 4 | 4 | 3 |
| (a) * | 4 | 5.6 | 1 | 2 | 2 | 1 | 3 | 4 | 2 | 1 | 3 | 2 | 3 |
| (b) * | 4 | 11.2 | 3 | 3 | 3 | 2 | 4 | 4 | 4 | 2 | 4 | 3 | 3 |
| (b) * | 4 | 5.6 | 4 | 2 | 1 | 2 | 4 | 4 | 2 | 1 | 2 | 1 | 3 |
| II * | 4 | 11.2 | 1 | 2 | 1 | 2 | 1 | 4 | 2 | 1 | 2 | 1 | 3 |
| * | 4 | 5.6 | 0 | 2 | 0 | 1 | 0 | 0 | 1 | 0 | 2 | 0 | 1 |
| III (c) * | 4(d) | 11.2 | 1 | 1 | 0 | 1 | 0 | 1 | 0 | 0 | 0 | 0 | 3 |
| * | 4 | 11.2 | 2 | 2 | 2 | 2 | 2 | 3 | 3 | 1 | 3 | 1 | 3 |
| * | 4 | 5.6 | 2 | 2 | 2 | 2 | 2 | 4 | 2 | 4 | 4 | 2 | 4 |
| IV * | 4 | 11.2 | 0 | 2 | 0 | 1 | 1 | 0 | 1 | 0 | 0 | 1 | 1 |
| V * | 4 | 11.2 | 0 | 1 | 0 | 1 | 0 | 2 | 0 | 0 | 0 | 0 | 1 |
| VI * | 4 | 11.2 | 2 | 2 | 2 | 3 | 0 | 4 | 2 | 2 | 2 | 2 | 3 |
| * | 4 | 5.6 | 2 | 2 | 0 | 1 | 1 | 1 | 2 | 1 | 1 | 0 | 2 |
| VII * | 4 | 11.2 | 2 | 2 | 1 | — | 1 | 4 | 2 | 1 | 3 | 2 | 3 |
| * | 4 | 5.6 | 1 | 2 | 1 | 1 | 1 | 3 | 1 | 0 | 2 | 2 | 3 |
| VIII * | 4 | 11.2 | 1 | — | 0 | 2 | 1 | 0 | 1 | 0 | 0 | 0 | 1 |
| * | 4 | 5.6 | 0 | 0 | 0 | 1 | 0 | 0 | 0 | 0 | 0 | 0 | 2 |
| IX * | 4 | 11.2 | 1 | 2 | 1 | 1 | 2 | 4 | 2 | 1 | 4 | 1 | 3 |
| X * | 4 | 11.2 | 1 | 1 | 0 | 2 | 2 | 1 | 1 | 1 | 0 | 0 | 1 |
| XI * | 4 | 11.2 | 2 | 3 | 2 | 4 | 4 | 3 | 2 | 2 | 4 | 4 | 3 |
| XII * | 4 | 11.2 | 2 | 3 | 2 | 2 | 2 | 3 | 2 | 1 | 2 | 1 | 3 |
| XIII * | 4 | 11.2 | 0 | 2 | 0 | 1 | 2 | 1 | 1 | 0 | 0 | 0 | 2 |

\* = herbicidal composition formulated immediately prior to treatment
(d) = spray volume 935 liters/hectare

TABLE II

| Compound of Example | WAT | kg/h | L | M | N | O | P | B | Q | D | R | E | F | C | J | S | K | T |
|---|---|---|---|---|---|---|---|---|---|---|---|---|---|---|---|---|---|---|
| I (a) * | 4 | 5.6 | 1 | 4 | 4 | 3 | 4 | 3 | 2 | 4 | 3 | 4 | 4 | 4 | 4 | 4 | 4 | 4 |
| (a) * | 4 | 1.12 | 0 | 2 | 0 | 0 | 3 | 2 | 1 | 2 | 1 | 3 | 3 | 1 | 0 | 2 | 3 | 3 |
| (b) * | 4 | 5.6 | 3 | 4 | 4 | 3 | 4 | 3 | 3 | 3 | 4 | 4 | 4 | 4 | 4 | 4 | 3 | 4 |
| (b) * | 4 | 1.12 | 0 | 0 | 0 | 0 | 2 | 2 | 0 | 2 | 0 | 0 | 2 | 2 | 1 | 4 | 3 | 3 |
| III (c) * | 4(d) | 5.6 | 1 | 0 | 1 | 0 | 2 | 2 | 0 | 2 | 0 | 1 | 1 | 1 | 0 | 2 | 2 | 3 |
| (c) * | 4(d) | 1.12 | 0 | 0 | 0 | 0 | 0 | 0 | 0 | 1 | 0 | 0 | 2 | 0 | 0 | 1 | 1 | 1 |
| * | 4 | 5.6 | 2 | 4 | 4 | 3 | 4 | — | 2 | — | 2 | 3 | 4 | 3 | 3 | 4 | 4 | 4 |
| * | 4 | 1.12 | 1 | 1 | 3 | 1 | 3 | — | 2 | 2 | 2 | 3 | 4 | 2 | 1 | 4 | 3 | 3 |
| * | 4 | 0.28 | 0 | 0 | 1 | 0 | 2 | — | 2 | — | 1 | 2 | 1 | 0 | 1 | 3 | 3 | 3 |
| VI | 4 | 5.6 | 2 | 4 | 4 | 1 | 4 | — | 3 | 3 | 4 | 2 | 4 | 2 | 4 | 4 | 3 | 4 |
| | 4 | 1.12 | 0 | 2 | 1 | 0 | 2 | — | 1 | 1 | 0 | 2 | 3 | 0 | 0 | 2 | 2 | 3 |
| VII | 4 | 5.6 | 2 | 4 | 3 | 2 | 3 | — | 3 | 2 | 4 | 4 | 4 | 3 | 3 | 4 | 4 | 4 |
| | 4 | 1.12 | 0 | 0 | 1 | 1 | 3 | 2 | 1 | 1 | 0 | 2 | 1 | 1 | 0 | 3 | 3 | 3 |
| VIII | 4 | 5.6 | 0 | 0 | 1 | 1 | 3 | — | 1 | 1 | 1 | 3 | 2 | 0 | 0 | 3 | 1 | 3 |
| IX | 4 | 5.6 | 0 | 0 | 0 | 0 | 2 | 3 | 0 | 2 | — | 1 | 2 | 0 | 0 | 2 | 3 | 3 |
| X | 4 | 5.6 | 1 | 0 | 0 | 0 | 1 | 1 | 0 | 2 | — | 2 | 1 | 0 | 0 | 2 | 2 | 3 |
| XI | 4 | 5.6 | 2 | 2 | 2 | 1 | 3 | 2 | 2 | 2 | 3 | 3 | 3 | 1 | 3 | 4 | 3 | 4 |
| | 4 | 1.12 | 1 | 0 | 0 | 0 | 2 | 1 | 1 | 1 | 0 | 2 | 1 | 0 | 0 | 2 | 1 | 2 |
| XII | 4 | 5.6 | 1 | 2 | 3 | 1 | 3 | 2 | 2 | 2 | — | 4 | 3 | 2 | 2 | 3 | 3 | 4 |

TABLE II-continued

| Compound of Example | WAT | kg h | Plant Species | | | | | | | | | | | | | | |
|---|---|---|---|---|---|---|---|---|---|---|---|---|---|---|---|---|---|
| | | | L | M | N | O | P | B | Q | D | R | E | F | C | J | S | K | T |
| | 4 | 1.12 | 1 | 0 | 0 | 0 | 1 | 2 | 1 | 1 | — | 1 | 1 | 0 | 0 | 2 | 1 | 2 |

\* = herbicidal composition formulated immediately prior to treatment
(d) = spray volume 935 liters/hectare

EXAMPLE XVII

This example illustrates pre-emergent activity of some of the compounds of this invention.

A good grade of top soil is placed in aluminum pans and compacted to a depth of ⅜ to ½ inch from the top of each pan. A pre-determined number of seeds and vegetative propagules of each of several plant species are placed on top of the soil in the pans. The seeds and propagules are covered with a measured amount of soil containing the herbicidal composition admixed throughout. The herbicidal composition is applied at the rate indicated by spraying the soil to be used as a cover layer, then thoroughly mixing the sprayed soil. The pans are placed on the sand of a greenhouse bench and watered as needed. The soil in the pans absorbs moisture through the apertured bottom of the pans. The plants are observed at the end of approximately 2 or 4 weeks (WAT) and the results recorded.

The pre-emergent herbicidal activity of the compounds of this invention is measured by the average percent control of each of the plant species. The average percent control is converted to a relative numerical scale for the sake of brevity and simplicity in the example. The pre-emergent herbicidal activity index used in the tables is defined as follows:

0 = 0 to 24% control
1 = 25 to 49% control
2 = 50 to 74% control
3 = 75 to 100% control

TABLE III

| Compound | WAT | kg h | Plant Species | | | | | | | | | | |
|---|---|---|---|---|---|---|---|---|---|---|---|---|
| | | | A | B | C | D | E | F | G | H | I | J | K |
| I (b) * | 4 | 11.2 | 3 | 2 | 3 | 3 | 3 | 3 | 0 | 2 | 0 | 3 | 2 |
| IV * | 2 | 11.2 | 3 | — | 0 | 0 | 0 | 0 | 0 | 0 | 0 | 0 | 0 |
| V * | 2 | 11.2 | 0 | — | 0 | 0 | 0 | 0 | 0 | 0 | 1 | 1 | 0 |
| XI * | 2 | 11.2 | 0 | 0 | 0 | 0 | 2 | 0 | 0 | 0 | 0 | 0 | 1 |

\* = herbicidal composition formulated immediately prior to treatment

TABLE IV

| Compound of Example | WAT | kg h | Plant Species | | | | | | | | | | | | | | |
|---|---|---|---|---|---|---|---|---|---|---|---|---|---|---|---|---|---|
| | | | L | M | N | O | P | B | Q | D | R | E | F | C | J | S | K | T |
| I (b)** | 2 | 5.6 | 0 | 3 | 0 | 0 | 0 | 0 | 3 | 1 | 0 | 3 | 2 | 1 | 0 | 1 | 1 | 2 |
| (b)** | 2 | 1.12 | 0 | 1 | 0 | 0 | 0 | 2 | 2 | 1 | 0 | 3 | 2 | 1 | 0 | 1 | 1 | 2 |

\*\* = spray volume 3740 liters/hectare - herbicidal composition formulated immediately prior to treatment For the sake of brevity and simplicity, the term "active ingredient" is employed hereinafter in this speicification to describe the ethanimidothioic (α-diaryloxyphosphinylmethylamino) acid ester hydrochloride derivatives of this invention, hereinbefore described.

In herbicidal compositions, the active ingredient can be admixed with one or more adjuvants which can be solid or liquid extenders, carriers, inert diluents (preferably which do not react with the ethanimidothioic acid esters), conditioning agents and the like. The herbicidal formulations comprise wettable powders, aqueous suspensions, dust formulations, emulsifiable oils and solutions in solvents. In general, these formulations can all contain one or more surface-active agents.

Surface-active agents which can be used in herbicidal formulations are well known to those skilled in the art and have been well documented in U.S. patents, bulletins and textbooks.

The preparation, formulations and particle size of the wettable powders, aqueous suspensions, dusts, emulsifiable oils and solutions in solvents are also well known to those skilled in the art and well documented.

The active ingredient is usually present in the herbicidal compositions in a range of about 0.5 to 95 parts by weight per 100 parts by weight of wettable or soluble powder, or wettable dust formulations; 5 to 95 parts by weight per 100 parts by weight emulsifiable oil formulations. A water formulation usually contains from 1 to 95 parts by weight of the active ingredient which can be further diluted for application. Formulations containing other than the above quantities of active ingredient can easily be prepared by those skilled in the art.

Application of the herbicidal compositions of this invention to the plant is well known to those skilled in the art. The application of liquid and particulate solid herbicidal formulations to the above-ground portions of the plants can be carried out by conventional methods, e.g., power dusters, boom and hand sprayers and spray dusters, however, since most of the compositions of this invention are water soluble, it is preferred to apply them in an aqueous medium.

The active ingredient can be admixed with one or more adjuvants which can be solid or liquid extenders, carriers, diluents, conditioning agents and the like to form herbicidal compositions. Herbicidal formulations have been described hereinbefore with particularity, it will be understood that various other modifications will be apparent to and can readily be made by those skilled in the art without departing from the scope and spirity of the invention. Accordingly, it is not intended that the scope of the claims appended hereto be limited to the examples and description set forth herein but rather the claims be construed as encompassing all the features of patentable novelty which reside in the present invention including all features which would be treated as equivalents thereof by those skilled in the art to which the invention pertains.

What is claimed is:

1. A compound of the formula

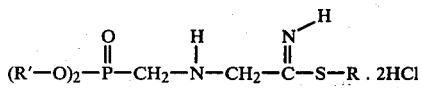

wherein R is selected from the group consisting of primary or secondary alkyl containing up to 10 carbons; phenyl; phenyl substituted with one or two groups individually selected from the class consisting of lower alkyl, lower alkoxy, halogen, nitro and trifluoromethyl; and lower alkyl substituted with naphthyl, phenyl or phenyl substituted with one or two groups individually selected from the class consisting of lower alkyl, lower alkoxy, halogen, nitro and trifluoromethyl; and R' is phenyl or a lower alkyl substituted phenyl group.

2. A compound as described in claim 1 wherein R' is phenyl.

3. A compound as described in claim 2 wherein R is ethyl.

4. A compound as described in claim 2 wherein R is phenyl or phenyl substituted with one or two groups individually selected from the class consisting of lower alkyl, lower alkoxy, halogen, nitro and trifluoromethyl.

5. A compound as described in claim 4 wherein R is p-chlorophenyl.

6. A compound as described in claim 2 wherein R is lower alkyl substituted with naphthyl, phenyl or phenyl substituted with one or two groups individually selected from the class consisting of lower alkyl, lower alkoxy, halogen, nitro and trifluoromethyl.

7. A compound as described in claim 6 wherein R is benzyl.

8. A compound as described in claim 6 wherein R is p-methoxybenzyl.

9. A herbicidal composition comprising a herbicidally acceptable surfactant, an inert diluent and a herbicidally effective amount of a compound of the formula

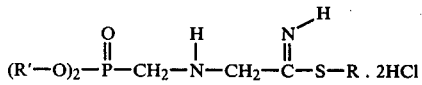

wherein R is selected from the group consisting of primary or secondary alkyl containing up to 10 carbons; phenyl; phenyl substituted with one or two groups individually selected from the class consisting of lower alkyl, lower alkoxy, halogen, nitro and trifluoromethyl; and lower alkyl substituted with naphthyl, phenyl or phenyl substituted with one or two groups individually selected from the class consisting of lower alkyl, lower alkoxy, halogen, nitro and trifluoromethyl; and R' is phenyl or a lower alkyl substituted phenyl group.

10. A composition as described in claim 9 wherein R' is phenyl.

11. A composition as described in claim 10 wherein R is ethyl.

12. A composition as described in claim 10 wherein R is phenyl or phenyl substituted with one or two groups individually selected from the class consisting of lower alkyl, lower alkoxy, halogen, nitro and trifluoromethyl.

13. A composition as described in claim 12 wherein R is p-chlorophenyl.

14. A composition as described in claim 10 wherein R is lower alkyl substituted with naphthyl, phenyl or phenyl substituted with one or two groups individually selected from the class consisting of lower alkyl, lower alkoxy, halogen, nitro and trifluoromethyl.

15. A composition as described in claim 14 wherein R is benzyl.

16. A composition as described in claim 14 wherein R is p-methoxybenzyl.

17. A method of controlling weeds and undesired plants which comprises contacting said plants with a herbicidal amount of a compound of the formula

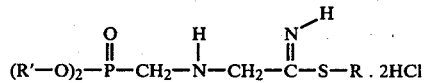

wherein R is selected from the group consisting of primary or secondary alkyl containing up to 10 carbons; phenyl; phenyl substituted with one or two groups individually selected from the class consisting of lower alkyl, lower alkoxy, halogen, nitro and trifluoromethyl; and lower alkyl substituted with naphthyl, phenyl or phenyl substituted with one or two groups individually selected from the class consisting of lower alkyl, lower alkoxy, halogen, nitro and trifluoromethyl; and R' is phenyl or a lower alkyl substituted phenyl group.

18. A method as described in claim 17 wherein R' is phenyl.

19. A method as described in claim 18 wherein R is ethyl.

20. A method as described in claim 18 wherein R is phenyl or phenyl substituted with one or two groups individually selected from the class consisting of lower alkyl, lower alkoxy, halogen, nitro and trifluoromethyl.

21. A method as described in claim 20 wherein R is p-chlorophenyl.

22. A method as described in claim 18 wherein R is lower alkyl substituted with naphthyl, phenyl or phenyl substituted with one or two groups individually selected from the class consisting of lower alkyl, lower alkoxy, halogen, nitro and trifluoromethyl.

23. A method as described in claim 22 wherein R is benzyl.

24. A method as described in claim 22 wherein R is p-methoxybenzyl.

* * * * *